(12) United States Patent
Chao

(10) Patent No.: US 10,045,540 B2
(45) Date of Patent: Aug. 14, 2018

(54) PEST CONTROL COMPOSITION

(71) Applicant: FAYETTEVILLE STATE UNIVERSITY, Fayetteville, NC (US)

(72) Inventor: Shirley Chao, Fayetteville, NC (US)

(73) Assignee: Fayetteville State University, Fayetteville, NC (US)

( * ) Notice: Subject to any disclaimer, the term of this patent is extended or adjusted under 35 U.S.C. 154(b) by 569 days.

(21) Appl. No.: 14/674,545

(22) Filed: Mar. 31, 2015

(65) Prior Publication Data

US 2015/0272131 A1 Oct. 1, 2015

(51) Int. Cl.
*A61K 36/00* (2006.01)
*A01N 65/08* (2009.01)

(52) U.S. Cl.
CPC .................................. *A01N 65/08* (2013.01)

(58) Field of Classification Search
CPC ...................................................... A61K 36/00
USPC ........................................................ 424/725
See application file for complete search history.

(56) References Cited

U.S. PATENT DOCUMENTS

| | | |
|---|---|---|
| 7,847,159 B2 | 12/2010 | Puzio |
| 7,888,388 B2 | 2/2011 | Mae |
| 7,951,565 B2 | 5/2011 | Ebneth |
| 7,982,095 B2 | 7/2011 | Puzio |
| 7,989,676 B2 | 8/2011 | Troukhan |
| 8,008,545 B2 | 8/2011 | Plesch |
| 8,017,839 B2 | 9/2011 | Napier |
| 8,049,064 B2 | 11/2011 | Cirpus |
| 8,101,213 B2 | 1/2012 | Baile |
| 8,106,244 B2 | 1/2012 | Burdick |
| 8,119,861 B2 | 2/2012 | Napier |
| 8,134,046 B2 | 3/2012 | Cirpus |
| 8,247,651 B2 | 8/2012 | Puzio |
| 8,258,371 B2 | 9/2012 | Napier |
| 8,273,958 B2 | 9/2012 | Napier |
| 8,298,794 B2 | 10/2012 | Swaller |
| 8,299,318 B2 | 10/2012 | Brover |
| 8,318,914 B2 | 11/2012 | Bauer |
| 8,324,455 B2 | 12/2012 | Puzio |
| 8,344,205 B2 | 1/2013 | Zank |
| 8,344,211 B2 | 1/2013 | Alexandrov |
| 8,362,325 B2 | 1/2013 | Troukhan |
| 8,373,024 B2 | 2/2013 | Cirpus |
| 8,426,206 B2 | 4/2013 | MuletSalort |
| 8,481,085 B2 | 7/2013 | Musty |
| 8,489,340 B2 | 7/2013 | Hames |
| 8,541,208 B1 | 9/2013 | Plesch |
| 8,592,646 B2 | 11/2013 | Portereiko |

FOREIGN PATENT DOCUMENTS

| | | |
|---|---|---|
| EP | 2601841 | 6/2013 |
| WO | 2008039362 | 4/2008 |

OTHER PUBLICATIONS

Adarkwah C, Obeng-Ofori D, Buttner C, Reichmuth C, Scholler M. Bio-ratiAdarkwah C, Obeng-Ofori D, Buttner C, Reichmuth C, Scholler M. 2010. Bio-rational control of red flour beetle *Tribolium castneum*(Herbst) (Coleptera: Tenebrionidae) in stored wheat with Calneem oil derived from neem seeds. Journal of Pest Science.2010. 83:471-479.

Athanassiou CG, Arthur FH, Throne JE. Efficacy of methoprene for control of five species of psocids (psocoptera) on wheat, rice, and maize. J Food Prot. Dec. 2010;73(12):2244-9.

Bhattacharya S , Virani S, Zavro M, Haas, G J. Inhibition of*Streptococcus mutans* and Other Oral streptococci by hop (*Humulus lupulus* L.) constituents. Economic Botany.2003; 57(1):118-12503.

Crippen T, Zheng L, Sheffield C, Tomberlin J, Beier R, Yu Z. Transient gut retention and resistence of *Salmonella* through metamorphosis in the lesser mealworm, *Alphitobus diaperinus*(Coleptera: Tenebrionidae).Journal of Applied Microbiology. 2012. 112: 920-926.

Darkling Beetle, accessed Feb. 17, 2015 at http://en.wikipedia.org/w/index.php?title=Darkling_beetle&oldid=646582020.

Hagstrum, D.W., P.W. Flinn, C.R. Reed and T.W. Phillips, 2008. Stored-grain insect areawide pest management. Paper No. 653, USDA-ARS/UNL Faculty. http://digitalcommons.unl.edu/usdaarsfacpub/653; 19 pages.

Lee, J. M., Park, S. M., Hwang, S., K, H. Y., Choi, G. Dietary Hempseed Meal Intake Increases Body Growth and Shortens the Larval Stage via the Upregulation of Cell Growth and Sterol Levels in *Drosophilia melanogaster*. Molecules and Cells. 2010. 29-36.

Mason, L. J., & McDonough, M. X. Biology, Behavior and Ecology of Stored Grain and Legume Insects. In Stored Product Protection. 2012.Manhattan, KS: Kansas State University.

Mason et al., Stored Grain Insect Pest Management, Purdue Extension Publication E-66-W; 2010; pp. 5.

McPartland John; Cannabis as repellent and pesticide; Journal of the International Hemp Association; 1997; 4(2): 87-92.

Natarajan, P.; Katta, S.; Andrei, I.; Ambati, V. Babu Rao; Leonida, M.; Haas, G.J. "Positive antibacterial co-action between hop (*Humulus lupulus*) constituents and selected antibiotics" Phytomedicine 2008; 15(3), 194-201.

Navarro S. The use of modified and controlled atmospheres for the disinfestation of stored products. Journal of Pest Science. 2012. 85:301-322.

Pandey K. N. Antifungal activity of some medicinal plants on stored seeds of Eleusine coracana. J. Indian Phytopathology. 1982. 35:499-501.

Parsons, Steps in Controlling Darkling Beetles, NC State University Cooperative Extension; Dec. 12, 2013, pp. 2; http://sampson.ces.nscu.edu/2013/12/steps-in-controlling-darkling-beetles-4/; accessed Feb. 19, 2015.

Schmalreck, A. F., M. Teuber, W. Reininger, and A. Hartl. Structural features determining antiobiotic potencies of natural and synthetic hop bitter resins, their precursors and derivatives. Canadian Journal of Microbiology. 1975; 21:205-212.

(Continued)

*Primary Examiner* — Michael V Meller
(74) *Attorney, Agent, or Firm* — Parsons Summa

(57) ABSTRACT

An insect control composition and related methods of preparation and use are disclosed. The composition includes a mixture of non-Cannabaceae flour and an amount of Cannabaceae seed flour effective to mitigate a population of Insecta treated with the mixture.

1 Claim, 5 Drawing Sheets

(56) References Cited

OTHER PUBLICATIONS

Shimwell J.L. On the relation between the staining properties of bacteria and their reaction towards hop antiseptic. Journal of the Institute of Brewing. 1937. vol. 43, pp. 111-118.

Steffey, K.L., and R.A. Weinzierl. 1991-2000. Insect pest management guide for stored grain. Originally published as C 1242. Illinois Natural History Survey Circular, Oct. 1989.

Triplehorn et al.; Ch. 26 Order Coleoptera: Beetles. Borror and DeLong's Introduction to the Study of Insects. 2005 7th edition. p. 436.

Veliky I. A. and K. Genest, Growth and metabolites of Cannabis sativa cell suspension cultures. Lloydia. 1972. 35:450-456.

Yigezu A. Yigezu, Corinne E. Alexander, Paul V. Preckel, D.E. Maier, C.P. Woloshuk, L.J. Mason, J. Lawrence, D.J. Moog, Optimal management of molds in stored corn, Agricultural Systems, Oct. 2008, vol. 98, Issue 3, pp. 220-227.

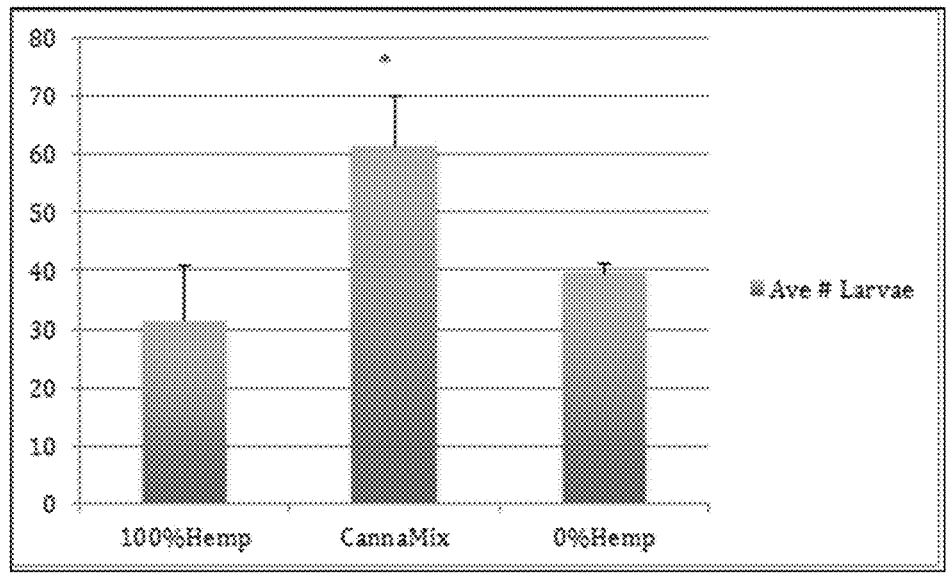
Figure 1. Average number of larvae produced by each mating pair following treatments.
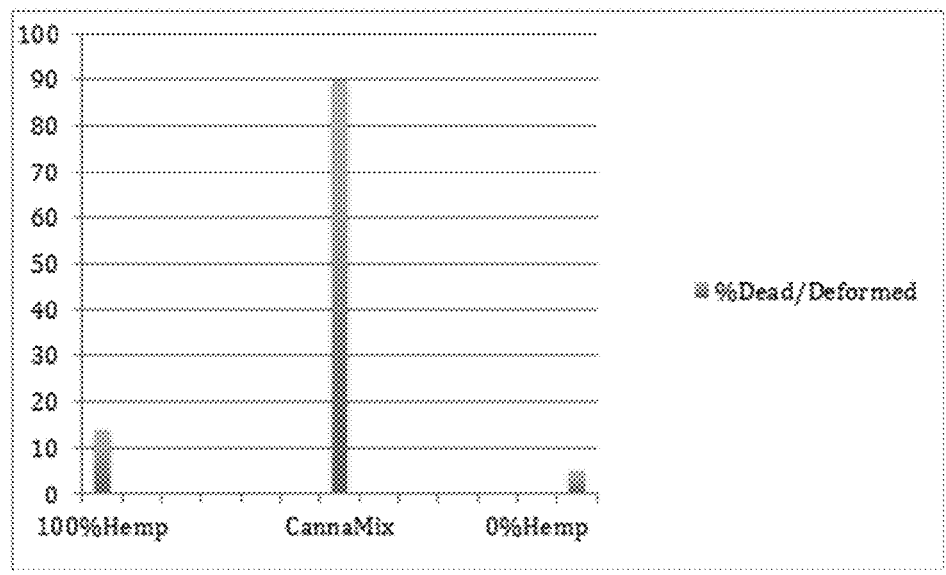
Figure 2. Percent of Dead/Deformed animals (all stages) following treatments.

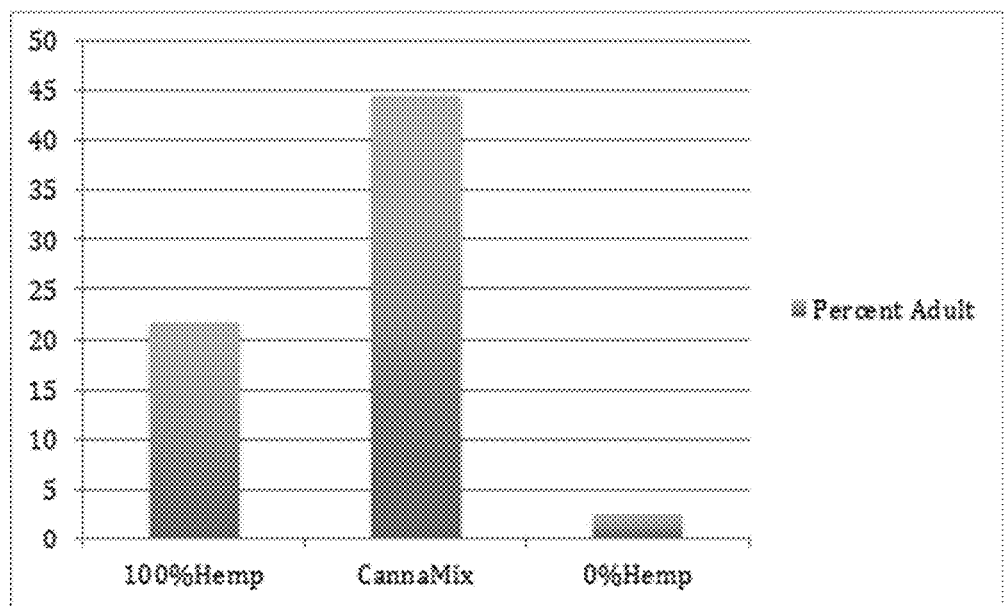
Figure 3. Percentage of progeny that developed into adult beetles after 60 days of treatment
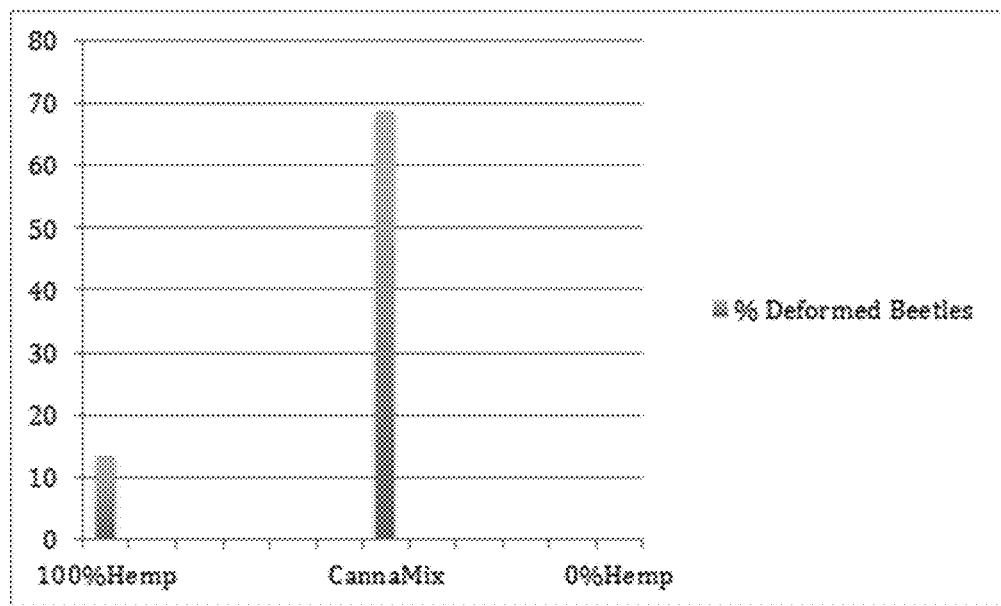
Figure 4. Percent of Dead/Deformed beetles (adult stage) following treatments.

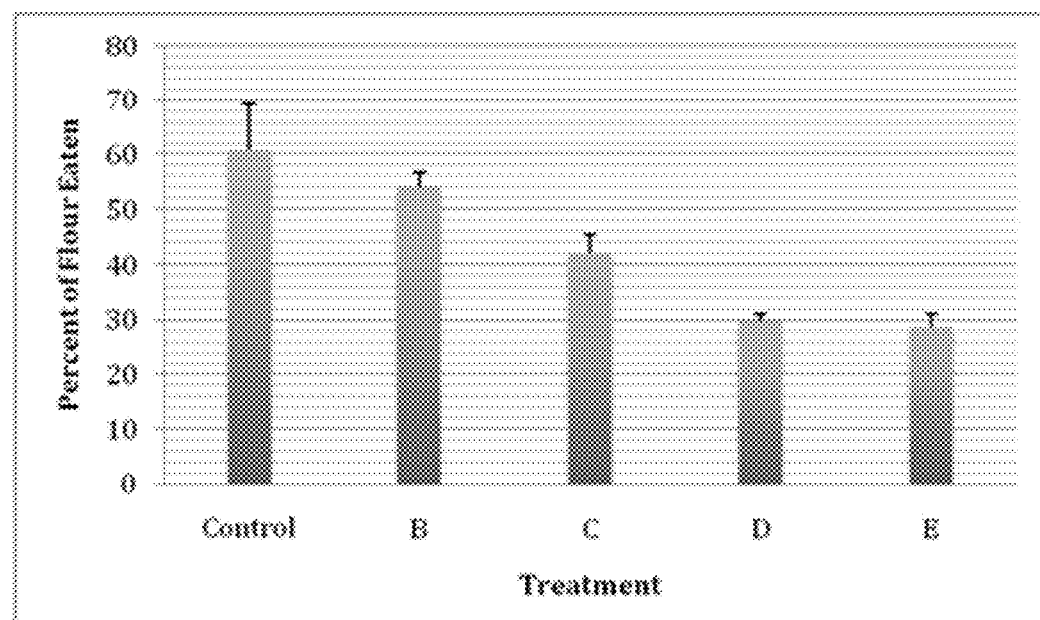
Figure 5. Percent of flour eaten by beetles raised on selected treatments after 7 days
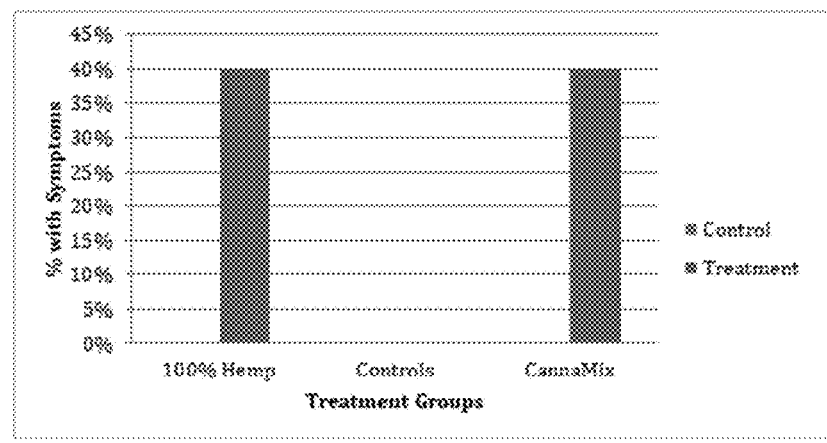
Figure 6. Percentage of larvae showing neurological symptoms following CPF exposure

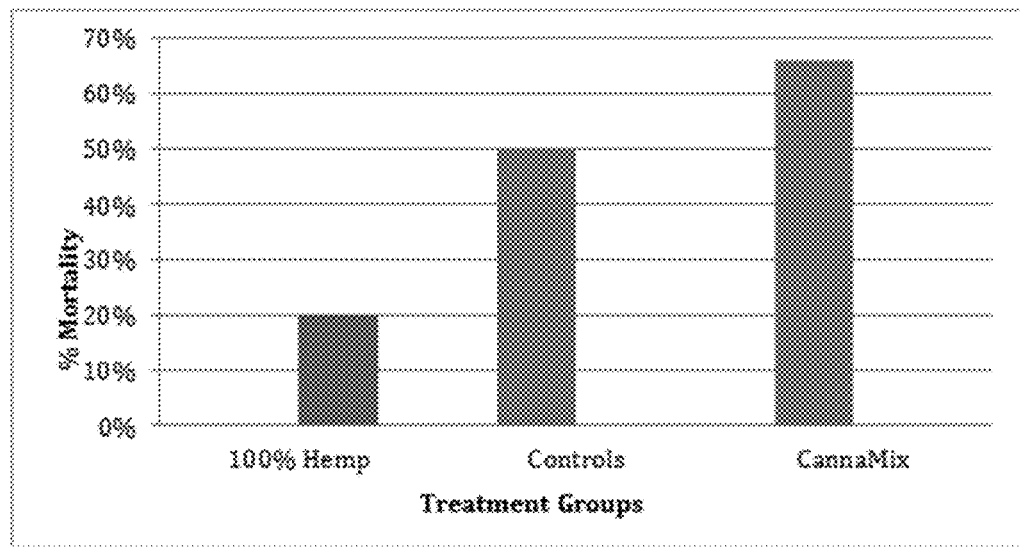
Figure 7. Percentage mortality of larvae following 16hrs of CPF exposure (20mg/L).
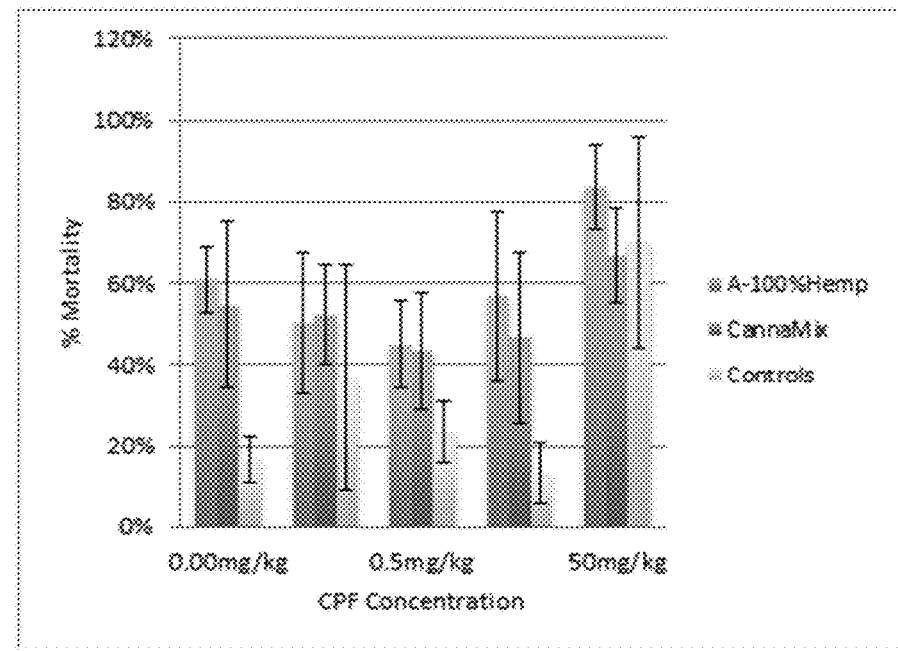
Figure 8. Percentage mortality of beetles fed on flour treatments following exposure to CPF concentrations

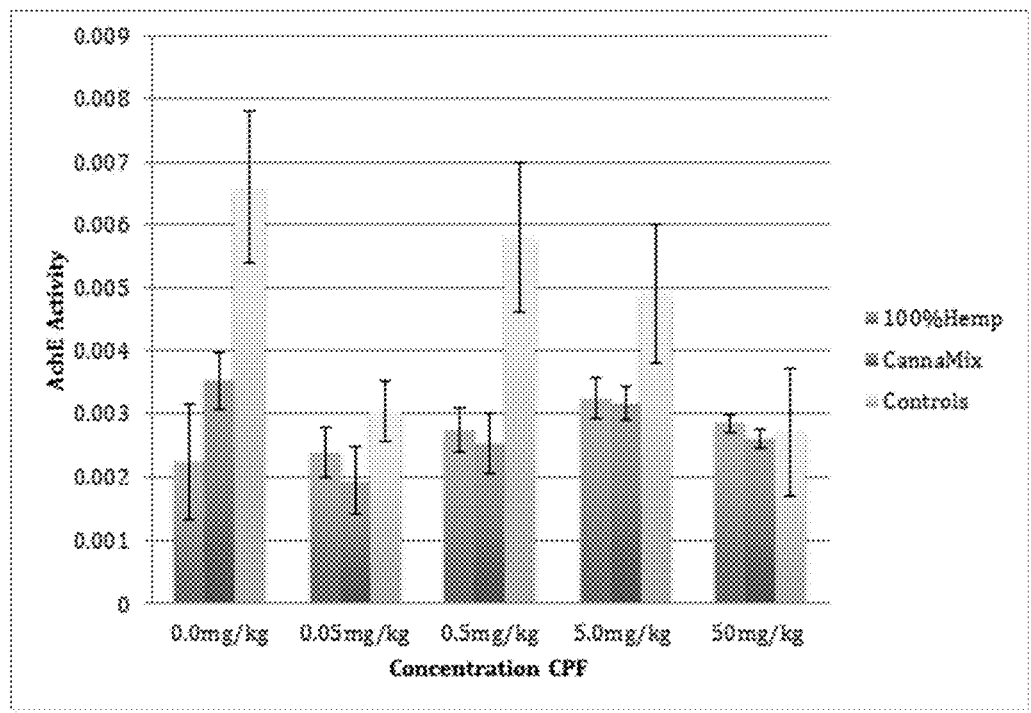
Figure 9. Acetylcholinesterase activity (standardized by total protein) of beetles fed three flour treatments

PEST CONTROL COMPOSITION

BACKGROUND

The present invention relates to the field of pest management, pesticides, and general pest control strategies.

Insect pests cause substantial damage to stored food products throughout the world and thus are considered major pests worldwide. Stored grain insect infestations rarely begin in the field and instead tend to develop from small numbers of pests already present in or around farm storage bins. Insects in stored grain affect grain quality; and therefore insects. Direct-feeding damage by insects reduces grain weight, nutritional value, and germination of stored grain. Insect pests also cause damage in humans and animals by their presence, either alive or dead, in grain that is to be processed for food. Investigations also cause contamination, odor, mold, and heat-damage problems that reduce the quality of the grain and may make it unfit for processing into food for humans or animals. For these and other reasons, the presence of pests above some de minimis amount is generally considered unacceptable in domestic grain supplies.

Small grains, including wheat, are harvested in spring and stored through the hottest and most humid months of the year. These conditions make it extremely difficult to prevent damage. Commercial grain buyers may refuse to accept delivery of insect contaminated grain, or may pay a reduced price. In the United States alone, the yearly post-harvest losses due to insects in corn and wheat are estimated at about $1.25 billion to $2.5 billion, accounting for 5-10% of the total value of corn and wheat produced (USDA, 2005).

The principal pests that cause damage are the adult and larval stages of beetles, and the larval stage of moths. Tenebrionidae ("darkling beetle") is a family of beetles that known to be one of the major pests in agricultural systems and products. The insects feed on durable stored products that humans use and consume such as cereals, cocoa beans and dried fruit. The presence of Tenebrionidae decreases the quality and quantity of such commercial food products, and in some cases they have depleted post-harvest food such as corn in developing countries by up to 10%. This is especially detrimental where food is scarce.

The darkling beetle is also a common problem in poultry facilities because the beetles tend to both consume the poultry feed and carry and transmit diseases to the poultry itself. Poultry is a leading agricultural industry in many states. For example, poultry is the number one agribusiness in North Carolina accounting for 110,000 jobs and generating an annual economic impact for North Carolina of $12.8 billion (NC Poultry Federation). Upon the infestation of a poultry house by relatively few of these insects, their numbers can extend into the millions within a few weeks. For example, a poultry house with 20,000 broiler chickens may be moderately infested by about 4 million beetles. During a typical 50 day grow-out period (i.e., the growth cycle for the fowl) these beetles can consume 400 pounds of poultry feed. Even more importantly, beetles may be carriers of pathogenic organisms, such as *E. coli, salmonella*, tapeworms, and cecal worms. According to the FDA, three common pathogens (*Salmonella, Listeria*, and *Toxoplasma*), are responsible for hundreds of human deaths and tens of thousands of hospitalizations every year.

One of the most common insecticides used to try to control insects in stored grain and other applications are in a class known as organophosphates. Although many organophosphates are important biochemicals, others are toxic to insects and animals, and some are the basis for nerve agents that can detrimentally affect humans. For this reason, organophosphates have been banned for use in home insecticide products in the US. Organophosphates are thought to degrade after application and thus widely used in agriculture, but health risks remain high for farmers, food-workers, and other non-target insects and animals that come in contact with the chemical in the environment.

Pyrethrum-based insecticides are the primary alternative to organophosphate insecticides. Pyrethrum has the advantages of it natural source and its low toxicity to humans (although larger amounts can affect the nervous system). As disadvantages, however, pyrethrum is a relatively high cost alternative, being imported primarily from East Africa and Australia; is a contact insecticide (i.e., requires direct contact with the pests); biodegrades in light; and is not persistent. Accordingly, many consumers are seeking safer, organic alternatives.

Accordingly a need exists for safer, more effective insecticides that target insect pests specifically without harming non-target animals and humans to continue to meet worldwide demands. Worldwide arable land per capita is declining, agricultural yield growth is slowing, and concerns about toxicity of many agricultural pesticides are increasing.

SUMMARY

In one aspect the invention is an insect control composition that includes a mixture of non-Cannabaceae flour and an amount of Cannabaceae seed flour effective to mitigate a population of insects treated with the mixture, and in particular is effective to mitigate a population of Tenebrionidae treated with the mixture.

In another aspect, the invention is a combination of a dried food product and a mixture of Cannabaceae flour and non-Cannabaceae flour. The proportion of Cannabaceae flour in the mixture is effective to mitigate a population of insects in the dried food product treated with the mixture.

In another aspect, the invention is a method of pest control that includes the steps of preparing a pesticide composition from a mixture of non-Cannabaceae flour and an amount of Cannabaceae seed effective to mitigate a population of Tenebrionidae treated with the mixture, and delivering the pesticide composition to the pest environment.

In yet another aspect, the invention is a method for preparing a pesticide composition effective to mitigate a population of Tenebrionidae when Tenebrionidae are treated with the composition. In this aspect, the invention includes the steps of grinding Cannabaceae seed into flour, and combining the Cannabaceae seed flour with non-Cannabaceae flour in a proportion effective to mitigate a population of Tenebrionidae when Tenebrionidae are treated with the composition.

The foregoing and other objects and advantages of the invention and the manner in which the same are accomplished will become clearer based on the followed detailed description taken in conjunction with the accompanying drawings.

BRIEF DESCRIPTION OF THE DRAWINGS

FIG. 1 shows the number of larvae produced following treatments with the invention as compared to those fed wheat flour and 100% hemp seed flour.

FIG. 2 shows the percent of dead or deformed animals (all stages) following selected treatments.

FIG. 3 shows the comparative percentage of progeny that developed into adult beetles after 60 days of treatment.

FIG. 4 shows the comparative percentage of dead or deformed beetles (adult stage) following treatments.

FIG. 5 shows the comparative percentage of flour eaten by beetles raised on the following treatments after 7 days FIG. 6 shows the comparative percentage of larvae showing neurological symptoms following CPF exposure.

FIG. 7 shows the comparative percentage mortality following CPF treatments after 16 hrs.

FIG. 8 shows the comparative percentage mortality of beetles fed on flour treatments following exposure to CPF concentrations.

FIG. 9 shows the comparative acetylcholinesterase activity (standardized by total protein) of beetles fed three flour treatments (100% Cannabaceae seed flour, the Cannabaceae flour/non-Cannabaceae flour composition, and controls containing wheat flour) mixed with CPF concentrations.

DETAILED DESCRIPTION

The invention is an organic product derived from a food additive that provides a safe, highly effective, low cost alternative for agricultural insect control. As an existing, known additive, the items in the formulation are classified by the federal government as 'generally regarded as safe', with minimal additional testing for regulatory purposes required. The product has been successfully tested for functionality in the lab using the darkling beetle, an insect whose physiological system is largely similar to other major insect pests.

The test results have indicated that the mortality rate associated with adult beetle consumption of the composition according to the invention is comparable to the beetle mortality rate associated with the highly toxic organophosphates (e.g., mortality approximately 60%). Moreover, the research shows that of the beetles which consume the inventive composition and survive, only 3.5% produce eggs which hatch, compared to a norm of 35%. In addition, most of the larvae which consume the composition of the invention either die before adulthood, or develop into deformed adults which cannot reproduce.

As used herein, the terms Tenebrionidae and "darking beetle" are used interchangeably, and the invention appears to be a successful pesticide for these and other insect families. The number of species in the Tenebrionidae is estimated at more than 20,000 and the family is cosmopolitan. Human transport has spread several individual species inadvertently (e.g., *Tribolium castaneum*), thus helping them become cosmopolitan.

The family Tenebrionidae not only includes a large number of species, but an immensely varied range of forms, and includes at least the following subfamilies: Alleculinae, Cossyphodinae, Diaperinae, Lagriinae, Nilioninae, Phrenapatinae, Pimeliinae, Stenochiinae, Tenebrioninae, and Zolodininae.

The Tenebrionidae are identified by a combination of features that include 11-segmented antennae that may be filiform, moniliform, or weakly clubbed, a first abdominal sternite that is entire and not divided by the hind coxae, and eyes notched by a frontal ridge. Tarsi have four segments in the hind pair and five in the fore and mid legs (5-5-4), tarsal claws are simple. (http://en.wikipedia.org/w/index.php?title=Darkling_beetle&oldid=646582020 accessed Feb. 17, 2015).

The invention is a new pesticide composed of flour made from Cannabaceae (10% to 90%), particularly hemp, and non-Cannabaceae flour. The main genera of the family Cannabaceae include the following: *Aphananthe, Cannabis L., Celtis L., Gironniera Gaudich., Humulus L., Lozanella Greenman, Parasponia Miguel, Pteroceltis Maxim, Trema Loureiro*. The seeds of Cannabaceae, when ground to form flour and mixed with another type of flour (in a specific ratio), as shown in FIG. 1, serve as a promising insecticide, particularly in stored products.

Mixtures of flour made from these genera serve as good potential insecticides as well as promising fungicides and antimicrobial agents. Cannabaceae mixtures can protect the all types of dried food products, including cereal products (flour, cake mix, cornmeal, rice, pasta, crackers, and cookies), dried beans, popcorn, nuts, chocolate, dried fruits, spices, tea, coffee, powdered milk, and cured meats. Cannabaceae mixtures can also protect other items such as pet food, birdseed, ornamental and decorative plant displays, dried flowers, and seeds.

Cannabaceae mixtures target insect pests at all stages (egg, larva, pupa, and adult). Major insect pests include genera from the following insect orders: Coleoptera and Lepidoptera. Cannabaceae mixtures also target various fungi that contaminate grains and produce mycotoxins that adversely affect human health. Fungal pests include the following filamentous fungi: *Fusarium, Myrothecium, Trichoderma*, and *Stachybotrys* genera. In addition Cannabaceae mixtures target various bacteria that contaminate and produce toxins such as: *Salmonella, Listeria, Escherichia, Clostridium*, and *Campylobacter* genera.

Cannabaceae mixtures serve as ideal pesticides in stored food products because they are known to be beneficial to humans when ingested. Cannabaceae seed is an exceptional nutritional food source packed with over 30% oil, 20-25% digestible proteins, over 20% fiber, as well as other essential fatty acids, vitamins and minerals. Studies have shown the ingestion of Cannabaceae by humans can: reduce risk of heart disease by lowering blood pressure and decreasing harmful cholesterol levels, reduce risk of diabetes by controlling blood sugar levels, and improving dermatological diseases.

In a broad aspect, the invention is an insect control composition comprising a mixture of non-Cannabaceae flour and an amount of Cannabaceae seed flour effective to mitigate a population of insects treated with the mixture.

More specifically, the invention is described herein in terms of the Tenebrionidae family of the Coleoptera order that can be mitigated with the mixture. A number of measurements can be used to determine the mitigation of any given population of insect (or pest; the terms are used substantially interchangeably herein). One measurement is the mortality, and in that sense, the mixture is effective to produce 60% mortality in representative populations of adult Tenebrionidae. The specific treatments and measured mitigation effects are set forth in the example portions of the specification.

Those of skill in this and related arts recognize that the amount of pesticide used in any given situation depends upon the individual circumstances; and there is generally no universal dosage or dosage ratio appropriate for all circumstances. Furthermore, effectiveness is not directly related to immediate results, and in some cases pesticides will have the desired effect within a few hours while in other cases a few days.

In some cases, the pesticide can be applied to an empty storage area before grain is added (e.g., before binning) while in other cases, the pesticide can be applied to or mixed with the grain as the grain is being stored. In other circumstances, pesticide can be applied as a "top-dress" after the grain has been binned, and in yet other circumstances, the stored grain can be examined or tested periodically and treated as needed. Depending upon the circumstances, several or all of these steps can be carried out on a particular portion of grain. Many University extension services provide helpful instructions for pest management, and exemplary (but not limiting) discussions are set forth in Parsons, "Steps in Controlling Darkling Beetles"; NC Cooperative Extension (http://sampson.ces.ncsu.edu/2013/12/steps-in-controlling-darkling-beetles-4/; accessed Feb. 19, 2015) or Mason and Obermeyer, "Stored Grain Insect Pest Management" Purdue Extension Publication E-66-W (2010).

In another sense, the mixture is effective to produce 90% mortality in adult Tenebrionidae, to reduce hatching in Tenebrionidae to no more than 3.5%, or to produce deformed adults (which either cannot reproduce or do not act as pests) in Tenebrionidae in a proportion of at least about 30%. In an exemplary embodiment, the mixture is effective to produce a combination of dead and deformed adult Tenebrionidae of at least about 60%.

As another potential measurement, the mixture is effective to reduce to feed intake of adult Tenebrionidae by factor of at least 50%. Measured in a comparative sense, the mixture is effective to mitigate a population of Tenebrionidae to the same extent as the same population would be mitigated by chlorpyrifos.

Expressed in yet another fashion, the mitigation will reduce the AchE activity of Tenebrionidae substantially the same as will 100% Cannabaceae flour.

With these results in mind, the effective amount of Cannabaceae seed flour in the mixture is typically between about 25% and 75% by weight of the mixture. The non-Cannabaceae flour can be any flour that does not otherwise adversely affect the composition or its mitigation effects. In exemplary cases, the pesticide mixture is typically put together with wheat flour, rice flour, or mixtures of wheat and rice flour. As set forth herein with respect to some of the examples, mixtures of 25% by weight of Cannabaceae seed flour in the mixture are effective, as are mixtures of 50% by weight or 75% by weight of Cannabaceae flour.

In another aspect, the invention is the combination of a dried food product and a mixture of Cannabaceae flour and non-Cannabaceae flour in which the proportion of Cannabaceae flour in the mixture is effective to mitigate a population of insects treated with the mixture.

As set forth elsewhere herein, exemplary dried food products include cereals, flour, cake mixes, cornmeal, rice, pasta, crackers, cookies, beans (dried), popcorn, nuts, chocolate, dried fruits, spices, tea, coffee, powdered milk, cured meat, pet food, bird seed, and mixtures of these items.

Expressed as the combination, the mixture of Cannabaceae flour and not help flour is made in a proportion effective to mitigate a population of Tenebrionidae when the combination is treated with the mixture. As in the other embodiments, an effective amount or proportion of Cannabaceae seed flour is between about 25% and 75% by weight of the flour mixture.

In another aspect, the invention is a method of pest control which includes the steps of preparing a pesticide composition from a mixture of non-Cannabaceae flour and an amount of Cannabaceae seed flour effective to mitigate a population of Tenebrionidae treated with the mixture, and then delivering the pesticide mixture to the pest environment.

Although a grain bin or silo is perhaps most exemplary, the pesticide can be delivered to fields, standing crops, buildings, storage bins, and combinations of these as the circumstances may require. Methods of distributing or delivering the composition can include spraying, dusting, sprinkling or baiting.

In some embodiments, the pesticide composition can be used in conjunction with other compositions or compounds that are toxic to the pests. Examples include organophosphate insecticides and carbamate insecticides.

In some embodiments of the method the pesticide is delivered to a grain storage area, typically one that has been cleaned to some extent, before the grain is added to the storage area. In another aspect, the pesticide composition can be delivered by mixing the pesticide composition with the dried food product—e.g., grain—while the product is being added to a storage area.

In other embodiments, the pesticide composition can be delivered after the grain has been binned, and in some circumstances, the pesticide composition can be delivered as a top dressing on binned grain. In most circumstances, the pesticide will be delivered using at least two, and potentially several or all, of these techniques to obtain the desired mitigation.

In another aspect, the invention is a method of preparing the pesticide composition and making sure that the composition is effective to mitigate the insects—e.g., Tenebrionidae—when the insects or pests are treated with the composition. In this aspect, the invention comprises the steps of grinding Cannabaceae seed into flour, and then combining the Cannabaceae seed flour with non-Cannabaceae seed flour in a proportion effective to mitigate the insect (e.g., Tenebrionidae) population when the insects are treated with the composition.

The effective proportions can be the same in this embodiment as in others; i.e., between about 25% Cannabaceae seed flour and about 75% Cannabaceae seed flour by weight in a mixture with wheat flour, rice flour, another appropriate flour, or some combination. Other exemplary flours include those made from barley, buckwheat, chick peas, corn (corn starch), corn meal, millets, oats, potatoes, rye and sorghum.

As recognized by those of skill in the art, the particle size distribution of the flour will have an effect on its storage and flow properties (as well as on its properties in end use). Accordingly, in appropriate embodiments the Cannabaceae seed flour and the non-Cannabaceae seed flour have substantially the same particle size distribution.

Those familiar with this art will also recognize that standard sieve opening sizes are frequently used to classify particle sizes and size distribution. In the case of flours and meals, the spacing of the grinding surfaces can be used to adjust the particle size distribution with (as would be expected) a larger opening between grinding services producing a more coarse meal and a smaller opening between grinding services producing a finer meal, relatively speaking.

The Cannabaceae family consists of eleven genera. Those skilled in the art will understand that hemp (i.e. *Cannabis*) is a genus of the plant family, Cannabaceae. Because hemp is one of the most widely available genera of Cannabaceae, the following examples were carried out predominantly using hemp (i.e. *Cannabis*). Based on these results, other genera of Cannabaceae are predictively expected to produce the same or substantially similar results.

EXAMPLES

Example 1: Disruption of Insect Reproduction and Development

Seeds of the *Cannabis* plant were purchased from various distributors in Canada. The seeds were cultivated grown and processed without chemical fertilizers or pesticides, and tested free of any chemical residue. No significant residues of Tetrahydrocannabinol (THC) were measured for the Cannabis seeds. All seeds were certified organic. Assorted wheat flour was purchased from various local distributors in Fayetteville, N.C. Insects were reared on wheat flour (0% Cannabaceae seed flour), Cannabaceae seed flour (100%, finely ground hemp seeds), and various ratios of hemp seed/wheat flour mixtures containing 25%, 50%, and 75% hemp seed.

Model Organisms

Larvae and adults of the Tenebrio species (darkling beetle) were purchased from Carolina Biological Supply Company (Burlington, N.C.). Animals were housed and raised on wheat germ and stored in an environmental chamber at a controlled temperature of 21° C. and humidity that ranged from 30-40% humidity.

Mating/Developmental Experiments

The larvae of the darkling beetles were observed daily anticipating the metamorphosis from larva to pupa. Once the larvae entered the pupa stage their sex was determined using a microscope. The pupae were then separated into groups according to sex and placed into labeled petri dishes which contained a small amount of wheat germ as well as a description of the sex of the insects, the number of insects, and the date the insects reaching the pupal stage. The petri dishes were placed into an environmental chamber where the temperature was set at 21° C. Each day the same procedure was performed for the larvae and the pupae. Approximately 8-12 days after the larva entered the pupal stage, the pupae began to transform into adult darkling beetles. Once the pupae entered the adult darkling beetle stage, they were immediately paired into male/female couples and each couple was randomly placed into one of three treatment groups: controls (0% Cannabaceae seed flour and 100% wheat flour), hemp seed flour (100%), and mixtures of hemp seed flour and wheat flour with varying ratios. The couples' habitats consisted of the assigned flour contained in a multi-purpose 2 oz. cup with a lid. Each couple also received 0.5 g of potato as a water source. In addition, holes were punched on the lids and sides of the mini cups to provide air to the insects. The cups were labeled with their treatment, the date the adults emerged from the pupa stage, and the date the adults were mated. The mating period lasted for a total of 14 days. After 14 days, the adult darkling beetles were removed from the 2 oz. container and placed into separate containers away from potential eggs or larvae (to prevent any cannibalism)

Four days after the adult darkling beetles were mated, microscopic inspection for eggs began. The adult beetles were removed from the flour during the inspection for eggs. Flour was poured from each container into a large petri dish and placed under a microscope where it was visually checked for eggs. The containers were checked thoroughly for eggs as well. In addition to checking for eggs, deaths among adult darkling beetles were also noted, and the dead beetles were removed. On the 12th day of mating, eggs were located at the bottom of the 2 oz. containers from at least one couple from each experimental group. Approximately 3 days after the 14-day mating period ended, first instar larvae were visible using a microscope from at least one couple from each experimental group.

To prevent harming the larvae, fish nets, sieves, and camel-hair brushes were used to separate the larvae from the flour treatments. The larvae were then placed into a small petri dish where they were counted and weighed using an analytical scale. Because the larvae were weighed in groups, it was necessary to determine the weight per insect, which was calculated by dividing the weight of all larvae by the total number of larvae counted.

The mating experiments were repeated at least three times with 4-7 replicates in each experiment. Comparison of the hemp seed flour and non-Cannabaceae seed flour composition and treatments with control compositions (0% Cannabaceae seed flour, 100% wheat flour) and with 100% hemp seed flour were conducted using T-tests for significant differences at $p<0.05$.

Results of Mating Experiments and Progeny

The couples were allowed to mate for 14 days, after which, the mating pairs were removed. Eggs were found in 92% of the 100% hemp seed treatment group, 75% of the 0% Cannabaceae seed group (controls) and 58% of the hemp flour/non-Cannabaceae flour composition group. Number of larvae (immatures) in the progeny was counted weekly as they developed into adult beetles. FIG. 1 shows number of larvae produced following treatments with the hemp flour/non-Cannabaceae flour composition was significantly greater than those fed wheat flour (0% Cannabaceae seed flour) and 100% hemp seed flour.

Significantly more larvae were produced by mating pairs exposed to the hemp flour/non-Cannabaceae flour composition compared to those exposed to 100% hemp and 0% Cannabaceae (wheat flour). Significant changes (noted by the asterisk) were based on paired T-test analysis with significance set at $p<0.05$.

After 60 days, final adult counts of the first generation (progeny) were noted. Approximately 90% of the progeny in the hemp flour/non-Cannabaceae flour composition treatments did not survive compared to 5% mortality in controls (0% Cannabaceae, 100% wheat flour) and 14% mortality in 100% hemp seed flour (FIG. 2). Less than 1% of insects in the 100% hemp seed treatments exhibited deformities. No deformities were observed in controls (0% Cannabaceae). Approximately 31% of the progeny in the hemp flour/non-Cannabaceae flour composition treatments exhibited deformities at the pupal or adult stage.

FIG. 2 illustrates the percent of dead/deformed animals (all stages) following treatments. Significant changes (noted by the asterisk) were based on paired T-test analysis with significance set at $p<0.05$. Data indicated a sample size of 283 (100% hemp), 394 (the hemp flour/non-Cannabaceae flour composition), and 345 (0% Cannabaceae).

In addition, insects in the hemp flour/non-Cannabaceae flour composition treatments developed at a faster rate than controls (0% Cannabaceae seed, 100% wheat flour) and 100% hemp seed treatments. Approximately 44% of progeny in the hemp flour/non-Cannabaceae flour composition developed into adults compared to 22% of insects in 100% hemp seed and only 2% in controls (0% Cannabaceae seed).

FIG. 3 illustrates the percentage of progeny that developed into adult beetles after 60 days of treatment: 100% hemp seed flour, the hemp flour/non-Cannabaceae flour composition, and 0% Cannabaceae seed flour (controls containing wheat flour).

FIG. 4 illustrates the percent of dead/deformed beetles (adult stage) following treatments. Although insects on the hemp flour/non-Cannabaceae flour composition developed faster than other treatments, deformities and mortality was higher in adults. FIG. 4 shows 69% of progeny that developed into adults either died or exhibited deformities that eventually led to deaths. Approximately 13% of 100% hemp seed treatments exhibited deformities and died. No deformities or deaths were observed in controls (0% Cannabaceae seed).

Example 2 The Hemp Flour/Non-Cannabaceae Flour Composition Disrupts Insect Feeding Feeding Experiments Adult darkling beetles were randomly placed into one of three treatment groups: controls (0% Cannabaceae seed flour and 100% wheat flour), hemp seed flour (100%), and the hemp flour/non-Cannabaceae flour composition. Treatments consisted of the assigned flour contained in a multi-purpose 1 oz. cup with a lid. Holes were punched on the lids of the mini cups to provide air to the insects. Each adult beetle was placed into a one ounce plastic cup containing 0.5 g of designated flour and a 2 cm diameter filter paper with 100 uL of distilled water. On days 1, 3, 5, and 7, each beetle was removed from the cup, flour was sieved to remove excess fecal matter and discarded exoskeleton, and flour and filter paper were weighed. Amount eaten was determined by subtracting the weight of the filter paper from the flour weight. Each adult beetle was placed into a one ounce plastic cup containing a known amount of flour treatment and a 2 cm diameter filter paper soaked with distilled water. Each plastic cup was covered with a lid with three holes to provide air for the beetles. Flour was weighed on days 1, 3, 5, and 7 days after sieving to remove excess fecal matter and discarded exoskeleton.

Results of Feeding Experiments

FIG. 5 illustrates the percent of flour eaten by beetles raised on the following treatments after 7 days: control (0% Cannabaceae), B (25% hemp seed mixed with wheat flour), C (50% hemp seed with wheat flour), D (75% hemp seed with wheat flour), E (100% hemp seed flour). After seven days, beetles ate significantly less flour in treatments containing at least 50% hemp seed flour (Treatments C, D, and E) compared to controls. Approximately 60.9% of the control flour was eaten by beetles compared to 28-30% eaten of flour containing Cannabaceae formulations (Treatments D and E).

Example 3 The Hemp Flour/Non-Cannabaceae Flour Composition Controls Beetles as Effectively as Chlorpyrifos (Organophosphate Insecticide)

Chlorpyrifos Exposure

Technical grade chlorpyrifos (99.7% purity; IUPAC name: O,O-diethyl O-3,5,6-trichloropyridin-2-yl phosphorothioate) was generously donated by DOW Agro Science (Indianapolis, Ind.). Chlorpyrifos (CPF) stock solutions were prepared in acetone. For dip assays, less than 0.02% of acetone was present in the total volume of the exposure cups to prevent any acetone toxicity.

Chlorpyrifos Dip Assays

Larvae from designated flour treatments were exposed to CPF (20 mg/L) by dipping 4 larvae at one time into CPF/acetone solutions for 30 seconds. Each larva ranged in size from 1.5-2 cm in length or 0.052 g to 0.131 g in weight and was at least 3rd instar larvae. Two inch plastic cups were used to dip the insects. Two replicates per concentration were tested for each experiment.

Results from Chlorpyrifos Dip Assay

Approximately 40% of insects in the 100% hemp seed flour treatments and the hemp flour/non-Cannabaceae flour composition treatments showed neurotoxic symptoms following exposure to CPF (FIG. 6). No symptoms were observed in the control groups.

FIG. 6 illustrates the percentage of larvae showing neurological symptoms following CPF exposure.

FIG. 7 shows the percentage mortality following CPF treatments after 16 hrs.

Chlorpyrifos Feeding Assays

For feeding assays, CPF was added to the flour treatments at the following concentrations: 0.0, 0.05, 0.5, 5.0 and 50 mg/kg body weight. Before exposure to chlorpyrifos, beetles were first acclimated to the three flour treatment (wheat flour, the hemp flour/non-Cannabaceae flour composition, and 100% hemp seed flour) for 24 hours. Control groups were exposed to the solvent containing acetone (less than 0.02%) and water mixed with designated flour treatment. Flour/CPF mixtures were prepared by mixing designated concentration of CPF/acetone with 2 g of flour into glass containers. Each glass of mixtures was shaken by hand for 1 minute to thoroughly mix the solution and flour. Flour mixtures were allowed to dry for 24 hrs. After 24 hrs, five beetles were added to a glass container with designated flour treatment and CPF concentration. The presence of symptoms was recorded after 24 hours of exposure. Mortality was recorded after 4 and 7 days. After mortality was determined, animals were frozen at −70 C until processed for protein and acetylcholinesterase assays.

Results from CPF Feeding Study

The hemp seed groups had significantly higher percentage of mortality compared to controls in the absence of CPF. FIG. 8 illustrates the percentage mortality of beetles fed on flour treatments following exposure to CPF concentrations (0, 0.05, 0.5, 5.0, 50 mg/kg). No significant differences were observed between flour treatments following exposure to the highest CPF concentration (50 mg/kg).

Acetylcholinesterase Assay

Whole beetles (control and treatment groups) were thawed and homogenized in 0.1M sodium phosphate (NaPO4) Buffer at pH 7. Tissues were homogenized using a polytron homogenizer (Powergen, Fisher Scientific, and Hanover Park, Ill.) for approximately 45 seconds. Tissues remained on ice during homogenization. The homogenate was then centrifuged for 5 minutes at 12,000 g and the supernatant was transferred for biochemical assays, specifically for total protein and AChE activity.

Total protein was determined by the Coomassie blue method using Bradford dye (Sigma-Aldrich, St. Louis, Mo., USA) and absorbance was measured at 595 nm. Bovine Serum Albumin (BSA) (Sigma-Aldrich, St. Louis, Mo., USA) was used as the standard. From each sample, approximately 20 µl of sample supernatant was used to measure protein content using the Bradford method (Bradford, 1976). The amount of absorbance was proportional to the amount of protein present.

Supernatants of homogenized samples were then measured for acetylcholinesterase activity using a modified assay by Ellman et al. (1961). In brief, acetylcholinesterase activity was measured from the supernatant, using acetylthiocholine iodide 98% (Sigma-Aldrich, St. Louis, Mo., USA) as the substrate in a 2 mL reaction medium consisting of 0.25 mM 5,5-dithio-bis(2-nitrobenzoic acid) or DTNB (Sigma-Aldrich, St Louis, Mo., USA), 0.1 M sodium phosphate buffer (Sigma-Aldrich, St. Louis, Mo., USA) at pH 7.5, and 0.001 M acetylthiocholine iodide. Absorbance was read at 412 nm at 3 minutes intervals up to 45 minutes.

Enzyme activities were standardized by total protein in the supernatant, as measured by the Bradford method described earlier. The AChE activity was replicated three times and repeated at least two times for each treatment.

Results of Acetylcholinesterase Assay

FIG. 9 illustrates the Acetylcholinesterase activity (standardized by total protein) of beetles fed three flour treatments (100% hemp seed flour, the hemp flour/non-Cannabaceae flour composition, and controls containing wheat flour) mixed with CPF concentrations (0, 0.05, 0.5, 5.0, 50 mg/kg).

In summary the invention will enable the agricultural industry to better protect crops from losses due to insects in a manner safe to humans and safe to the environment. In addition to less food waste due to insect contamination, health benefits will accrue from reduced pesticide residues on food. Agricultural workers will receive a direct beneficial impact, as it is these workers that currently have the greatest prolonged exposure to the harmful pesticides currently being applied. The invention provides the additional impact of safer and healthier poultry operations In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A method of killing or deforming beetles in a pest environment consisting essentially of preparing a pesticide mixture consisting essentially of 75% hemp flour and 25% of a wheat and rice flour mixture; delivering the pesticide mixture to a pest environment selected from the group consisting of buildings, storage bins, and combinations thereof; storing a dried food product selected from the group consisting of cereal products, flour, cake mix, cornmeal, rice, pasta, crackers, cookies, dried beans, popcorn, nuts, chocolate, dried fruits, spices, tea, coffee, powdered milk, cured meat, pet food, birdseed, and mixtures thereof with the pesticide mixture in the selected pest environment; and wherein the proportion of the pesticide mixture present with the stored food product is effective to kill or deform beetles in the dried food product stored with the pesticide mixture.

* * * * *